United States Patent [19]

Wood et al.

[11] Patent Number: 4,849,346

[45] Date of Patent: Jul. 18, 1989

[54] METHOD FOR DETERMINING THIOREDOXIN REDUCTASE ACTIVITY

[75] Inventors: John M. Wood; Karin U. Schallreuter, both of Mound, Minn.

[73] Assignee: Regents of the University of Minnesota, Minneapolis, Minn.

[21] Appl. No.: 13,671

[22] Filed: Feb. 12, 1987

[51] Int. Cl.[4] .......................... C12Q 1/26; C12Q 1/00; C12N 13/00; G01N 24/00
[52] U.S. Cl. .................................. 435/25; 435/4; 435/173; 436/173; 436/803; 436/56; 436/63; 436/64
[58] Field of Search ............................. 435/4, 25, 173; 436/173, 803, 56, 62, 149, 806, 63, 64; 128/653, 654

[56] References Cited

PUBLICATIONS

K. U. Schallreuter et al., *Biochem. Biophys. Res. Commun.*, 136, 630 (1986).
K. U. Schallreuter et al., *Biochem. Biophys. Res. Commun.*, 135, 221 (1986).

*Primary Examiner*—Robert J. Warden
*Assistant Examiner*—Toni R. Scheiner
*Attorney, Agent, or Firm*—Merchant, Gould, Smith, Edell, Welter & Schmidt

[57] ABSTRACT

The present invention provides a method for measuring the activity of thioredoxin reductase in mammalian cells by contacting the cells in vivo or in vitro with a quaternary ammonium salt spin-labelled with a stable nitroxide free radical, and measuring the rate of reduction of the uncomplexed nitroxide free radical at the cell surface by electron spin resonance. This rate of reduction provides a measure of thioredoxin reductase activity at the surface of the cells.

5 Claims, 2 Drawing Sheets

METHOD FOR DETERMINING THIOREDOXIN REDUCTASE ACTIVITY

This invention was made with the assistance of Grant No. AM18101, awarded by the National Institutes of Health. The Government has certain rights in this invention.

BACKGROUND OF THE INVENTION

Oxygen radicals are known to cause a number of disruptive processes at the cellular level. These include lipid peroxidation, alterations of enzyme activity, cleavage of DNA, cell mortality, and polymerization of polysaccharides. Furthermore, oxygen radicals can be generated by a number of physical or biological processes (e.g., enzymatically, photochemically, radiochemically, etc.). It is now well recognized that oxygen radicals are important mediators in the toxicity of chemical substances. For example, compounds which produce oxygen radicals have been shown to act as tumor promoters. Multiple defense mechanisms have evolved for coping with oxidant toxicity at the cellular level. Enzymes such as superoxide dismutase, catalase and other peroxidase (e.g., glutathione peroxidase) remove oxygen radicals and anions. Also reactive radicals such as OH· and $O_2.-$ can be removed by small radical-trapping molecules such as Vitamin A, C and E and by thiols such as reduced glutathione.

Therefore, a need exists for methods to determine the ability of mammalian cells to resist the internalization of free radicals, such as the oxygenderived free radicals generated by the action of ultraviolet (UV) light on the skin. Such methods can be used to determine the efficacy of therapeutic antioxidants and to diagnose pathologies which alter oxidant removal pathways in vivo.

SUMMARY OF THE INVENTION

The present invention provides a method for measuring the activity of the enzyme thioredoxin reductase (TR) in mammalian cells comprising:

(a) contacting the cells with a hydrophobic quaternary ammonium salt comprising a stable nitroxide free radical (a nitroxide "spin label"); and (b) applying the techniques of electron spin resonance (EPR) to determine the rate of reduction of the nitroxide free radical of the uncomplexed quaternary ammonium salt at the cell surface; said rate of reduction providing a measure of the thioredoxin reductase activity at the surface of the cells.

The method of the present invention is particularly effective to measure the activity of surface thioredoxin reductase in the case of skin cells, e.g., epidermal cells such as normal and malignant melanocytes. This activity has been found to correlate to the ability of the cells to eliminate, and thus to resist, damage by free radical oxidants. Furthermore, the level of TR activity can be employed as a diagnostic indication of certain pathological conditions. For example, melanomas exhibit substantially higher levels of TR activity than do normal skin cells.

The present invention is based upon our discovery that guinea pig epidermis contains an extremely reactive nitroxide reductase, which rapidly reduces uncomplexed spin-labelled quaternary ammonium salts ("quats"). This catalytic activity was confirmed to be enzymatic by the inhibition of the reduction of the spin label by the topical application of thioenzyme inhibitors to the skin cells. After the enzymatic reduction of the paramagentic nitroxide to the reduced secondary amine product, the remaining EPR spectrum was found to represent only cell surface-bound spinlabelled quat. The nitroxide reductase was determined to be thioredoxin reductase (TR) by experiments in which TR was isolated from human keratinocytes and found to rapidly reduce a spin-labelled quat in vitro.

Therefore, the present method assays the ability of the thioredoxin/thioredoxin reductase system to reduce potentially harmful free radicals. The structures and mechanism of action of these two thioproteins are well understood at the molecular level. The reduction of the stable nitroxide free radical on the spin-labelled quaternary ammonium salt yields a secondary amine as the principle reaction product. This is consistent with the involvement of an enzymic thiyl radical (—SH) in the reaction mechanism. A similar reaction pathway can be formulated for the reduction of $O_2.-$ wherein fully reduced thioredoxin transfers four electrons of two molecules of $O_2.-$ to give two molecules of water and one peroxide anion ($O_2^{2-}$) as the reaction products. In both cases, thiyl radicals in thioredoxin reductase are converted to disulfide (—S—S—) moieties when the enzyme is oxidized. See K. U. Schallreuter et al., Biochem. Biophys. Res. Commun., 136, 630 (1986), the disclosure of which is incorporated by reference herein.

Based on our experiments which demonstrate that reduced TR inhibits tyrosinase activity, a connection between the reduction of UV-generated radicals (R.) by thioredoxin reductase and melanin biosynthesis is suggested. Since UV light increases the concentration of radicals at the surface of keratinocytes, available electrons would be expected to be consumed in free radical reduction rather than in thioredoxin reduction. Under those conditions, the equilibrium between oxidized and reduced thioredoxin would provide more of the oxidized thioredoxin in the cell. This would cause a direct increase in tyrosinase activity and a corresponding increase in melanin biosynthesis.

However, in the absence of UV light, more electrons would be expected to be applied toward thioredoxin reduction in the cell. This would directly inhibit melanin formation. These relationships are summarized in Table I, below.

TABLE I

| | Relative Level of Cellular Parameter | | | | |
|---|---|---|---|---|---|
| Activity of Membrane-Associated TR* | Rate of Reduction of Free Nitroxide | Level of R. Penetration into Cell | Thioredoxin Oxidation State | Tyrosinase Activity | Melanin Formation |
| Low[a] | Low | High | Oxidized | High | High |
| High[b] | High | Low | Reduced | Low | Low |

*TR = Thioredoxin Reductase
[a]TR primarily oxidized (—S—S—)
[b]TR primarily reduced (—SH HS—)

Therefore, the location and activity of thioredoxin reductase indicates that this enzyme provides a free radical defense mechanism to prevent free radical permeation into cellular lipids where lipid peroxidation can lead to cell damage or cell death. A preliminary study of TR activity on the skin of 28 human volunteers, as well as on 13 patients with vitiligo (without other systemic disorders) has further demonstrated that the function of the enzyme may be correlated with free radical production from UV light (data not shown).

BRIEF DESCRIPTION OF THE DRAWINGS

FIG. 1(B) depicts the EPR spectrum of bound spin-labelled quat (2) on guinea pig epidermis.

DETAILED DESCRIPTION OF THE INVENTION

Figure 1:
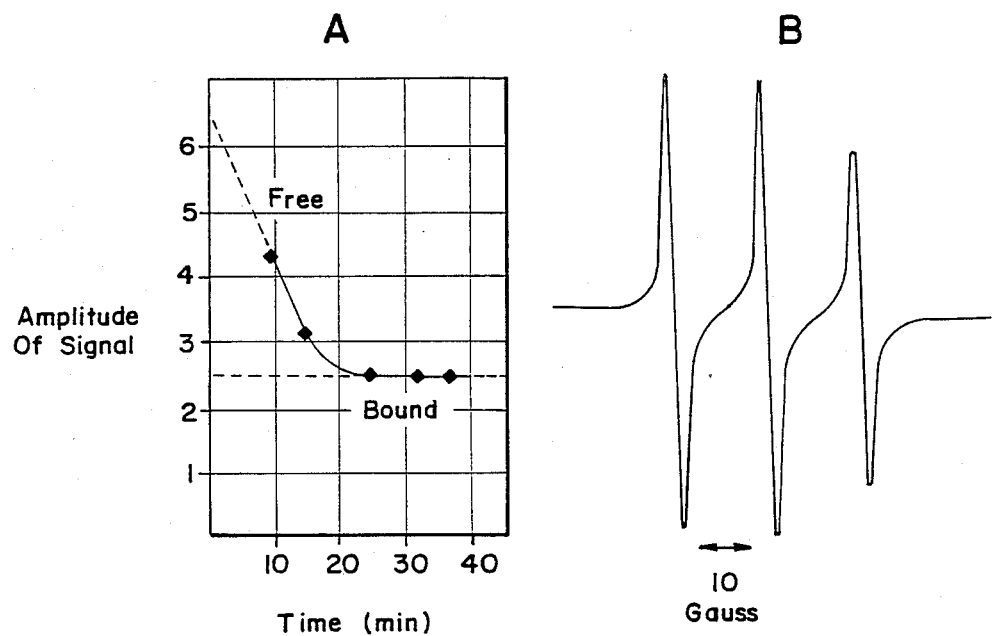
FIG. 1 (A) is a graphical depiction of the enzymatic reduction of free spin-labelled quat 2 by guinea pig epidermis in vivo.

The present method comprises a first step of contacting a portion of mammalian cells with a hydrophobic quaternary ammonium salt which incorporates a stable nitroxide free radical. The assay can be conducted in vivo by first exposing a section of the exposed tissue of the subject to a solution of the labelled quat in a suitable solvent such as aqueous ethanol. Following evaporation of the solvent, a sample of treated tissue can be isolated by a standard biopsy technique, and washed to remove superficiallybound quat, e.g., with a physiological salt solution. Cells grown in tissue culture can also be assayed by the present method. The treated tissue can then be placed directly in an EPR cell and the signal intensity decrease monitored over time. The slope of the curve obtained by plotting the decrease in EPR signal intensity against time provides a measure of the rate of reduction of the nitroxide spin label which can be directly correlated to the level of TR activity present at the surface of the cells. Thus, comparisons of relative TR levels in various types of cells, such as normal and neoplastic skin cells, can readily be accomplished.

Preferred nitroxide radical-containing ("spin-labelled") quaternary ammonium salts are those of structure I:

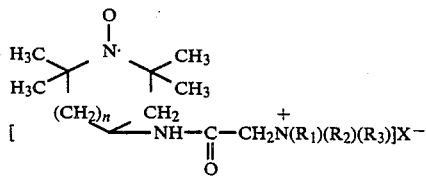

wherein n is 0 or 1, $X^-$ is an equivalent amount of a pharmaceutically-acceptable anion such as $Cl^-$, $Br^-$, $1^-$, $SO_4^{-2}$, $PO_4^{-3}$, $^-OAc$ and the like, and wherein $R_1$, $R_2$ and $R_3$ are substituents which render the spin-labelled quat sufficiently hydrophobic so that it can interact sufficiently with the cell membrane, e.g., can react at the surface of a lipid bilayers. For example, the spin-labelled quat preferred for use in the present method can be represented by formula I, wherein n=1, $X^-$ is a halogen anion such as $Br^-$, $R_1=R_2=$methyl and $R_3$ is benzyl.

Typically, $R_1$ and $R_2$ will be H, $(C_1-C_4)$alkyl, hydroxy$(C_1-C_4)$alkyl, benzyl or pyridyl and $R_3$ will be $(C_8-C_{22})$alkyl, $(C_8-C_{22})$alkylamido$(C_1-C_5)$alkyl, phenyl, benzyl, phenyl$(C_2-C_5)$alkyl, $[(C_1-C_{12})(\text{alkyl})_{1-2}$phenyl-]or $[((C_1-C_2)\text{alkyl})_{1-2}\text{phenyl}(OEt)_{1-5}]$. However, it is to be appreciated that any given spin-labelled quat of formula I can be readily tested for its suitability for use in the method of the present invention simply by contacting it with a sample of the target cells, and measuring the rate of decrease of the amplitude of the resultant EPR signal, if any.

Spin-labelled quats of formula I wherein X is a halogen anion can be prepared by reacting 4-(2-haloacetamido)-2,2,6,6-tetramethyl-piperidine-N-oxyl or 3-(2-haloacetamido)-2,2,5,5-tetramethyl-pyrrolidine-N-oxyl with an amine of the formula $N(R_1)(R_2)(R_3)$ in a suitable solvent such as a lower alkanol. The starting materials 4-(2-bromoacetamido)-2,2,6,6-tetramethyl-piperidine-N-oxyl and 3-(2-bromoacetamido)-2,2,5,5-tetramethyl-pyrrolidine-N-oxyl are available from Sigma Chemical Co., St. Louis, Mo. Suitable primary, secondary and tertiary amines are commercially available from many sources, e.g., from Aldrich Chemical Co., Milwaukee, Wisc.

The invention will be further described by reference to the following detailed example.

EXAMPLE I

ENZYME ASSAYS

A.

Materials and Methods

1. Enzymes

Tyrosinase, NADPH, and NADP+ were obtained from Sigma Chemical Co., St. Louis, Mo. ADPSepharose was obtained from Pharmacia, Upsala, Sweden. *E. coli* thioredoxin reductase and thioredoxin were generous gifts from out colleague, Dr. F. K. Gleason. Cell cultures of differentiated human keratinocytes were provided by Dr. M. Pittlekow, Mayo Clinic, Rochester, Minn.

2. Preparation of 4-Bromoacetamido-2,2,6,6-tetramethylpiperidine-N-oxyl (1)

Following the procedure of Weaver and Whaley *J. Amer. Chem. Soc.*, 69, 515 (1947), 1.0 g (6.3 mmoles) of crude 4-amino-2,2,6,6-tetramethylpiperidine-N-oxyl and 10 ml reagent grade dichloroethylene was placed in a 25 ml, 2 neck, round bottom flask fitted with a dropping funnel, magnetic stirring and a drying tube. Practical grade bromoacetylbromide 0.15 g (0.28 ml, 3.2 mmole) dissolved in 5 ml $CH_2Cl_2$ was added dropwise over a 15 min. period to the stirred reaction mixture which was maintained at $-10°$ C. After the addition of the acid bromide was complete, the temperature was raised to 25° C., and the reaction stirred for 15 min. The reaction mixture was extracted with $3\times10$ ml portions of 5% aqueous hydrochloric acid (HCl). The aqueous extracts were combined and extracted with 2 x 10 ml portions of CH$_2$Cl$_2$ which were combined with the previous organic phase. The organic phase was dried over anhydrous MgSO$_4$ and evaporated to dryness. The residue was recrystallized from benzene-hexane to give product (1) as orange needles. Analysis: calculated for C$_{11}$H$_{20}$N$_2$: C, 45.2%; H, 6.85%; N, 9.5%; Found C, 46%; H, 6.79%; N, 9.44%. M.P. 123°–4° C. Molecular ion in mass spectrometer, calculated: 292; observed: 292.

3. Preparation of 3-(Dimethyl-benzyl-amino)acetamido-2,2,6,6-tetramethylpiperidine-N-oxyl bromide (2)

Dimethylbenzylamine (1.0 g) (Aldrich Chem. Co.) was dissolved in 50 ml of dry methanol and 0.8 g 4-bromoacetamido-2,2,6,6-piperidineN-oxyl (1) was added. The reaction mixture was refluxed for five hours, cooled and 250 ml of dry diethylether added. Pale yellow crystals formed immediately. They were isolated by filtration, washed with diethyether and dried over P$_2$O$_5$ to yield product 2 (Formula I, n=1, R$_1$=R$_2$=H, R$_3$=benzyl, X$^-$=Br$^-$). The EPR spectrum of spin-labelled quat, 2 as determined on a Varian E4 spectrometer at 25° C., gave $a$N values of 17.2 gauss as compared with 17.0 gauss for the free reagent 4-bromoacetamido-2,2,6,6-tetramethylpiperidine-N-oxyl (ATEMPO). Line widths of 1.87, 1.87 and 2.20 gauss were recorded with the low field line being broadest. This low field line decreased in intensity and broadens further upon complexation of 2 to cell surfaces.

4. Animals Female albino guinea pigs (non-pregnant), under three months of age with a body weight of approximately 400 g, where chosen for the studies performed herein. Pirlbright white and compatible white guinea pigs were from Camm Research, N.J.

B.

Electron Spin Resonance Experiments

1. In Vivo Thioredoxin Reductase Assays in Skin

Thioredoxin reductase activity was monitored in vivo and in vitro by following the decrease in amplitude of the nitroxide radical signal with time when spin-labelled quat (2) was applied as the radical substrate. All spectra were recorded on a Varian E-4 Spectrometer at 25° C.

For in vivo electron spin resonance experiments, 0.05 ml of spin-label (5% solution) was applied epicutaneously to shaved guinea pigs in a (1:1) solution of ethanol-water. This concentrated solution was chosen to ensure that binding sites at cell surfaces are saturated in the short duration for exposure to spin-labelled quat. Punch biopsies (4 mm) were taken immediately after evaporating the solvent from the surface of the skin. The area covered with spin-label was approximately 1.0 cm in diameter. Superficially-bound spin-label was washed from each biopsy with isotonic saline (0.9% NaCl) for 5 minutes. The tissue biopsy was then placed directly in the EPR cell and the fate of the spin-label was followed with time until only residual bound nitroxide radical signal remained.

FIG. 1, Panel A is a plot of the amplitude of the EPR signal against time. The residual signal represents bound spin-labelled quat, which is not available for enzymatic reduction. Panel B depicts the EPR spectrum of bound spin-labelled quat 2 on guinea pig epidermis. This bound EPR spectrum shows line broadening from 11 gauss (free spin-label) to 18 gauss (bound spin-label) in the central resonance. The high field line is broadened and decreased in amplitude which is indicative of surface complexation with some freedom for rotation of ths spin-labelled group.

Tissues retaining bound spin-label were incubated with 1% solutions of aryltrimethyl ammonium chloride (Lonza Inc., Fairlawn, NJ) and benzyl dimethyl-2-methyl-4-(1,1,3,3-tetramethyl-butyl-phenoxy-ethoxyethyl ammonium chloride) for exchange reactions. Any residual complexed spin-label was removed from the biopsies by incubation for 5 minutes in 80% trichloroacetic acid.

Following these preliminaary experiments, the nitroxide reductase was also found in biopsies taken from human skin. The EPR spectra obtained for a typical in vivo bioassay from 3 mm punch biopsy of epidermis is presented in FIG. 2. The reduction of the free spin-label on the surface of the skin can be followed by monitoring the decrease in the intensity of the signal with time until only bound nitroxide radicals remain after 43 minutes. 2. In Vitro Thioredoxin and Thioredoxin Redutase Assays In vitro assays were performed in quartz tubes in KH$_2$PO$_4$ buffer 0.1 M, pH 7.2 with purified thioredoxin reductase from E. coli and from human keratinocytes. Reactions were started by adding spin-labelled quat 2 and NADPH (50 μmoles). Prior to the EPR experiments, thioredoxin reductase activity was checked by the insulin disulfide reduction assay [N. E. Engstrom et al., *J. Biol. Chem.*, 249, 2263 (1980)].

Thioredoxin reductase from adult human keratinocytes was purified by affinity column chromatography by complexation of this flavoprotein to ADP-sepharose followed by elution with 10 mM NADP+pH 7.2. Tyrosinase was assayed spectrophotometrically by following the increase in absorbancy at 280 nm with 10 μmoles of L-tyrosine as substrate in 0.5 M oxygenated KH$_2$PO$_4$ buffer 6.5. A three-minute lag occurs before linear kinetics ensue.

Figure 2:
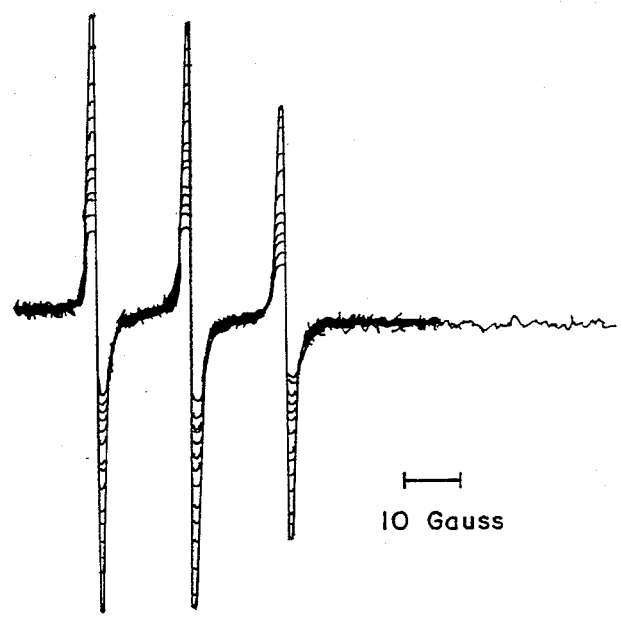
FIG. 2 depicts EPR spectra showing the sequential reduction of a spin-labelled quat bound to the surface of human epidermis in vitro.
Figure 3:
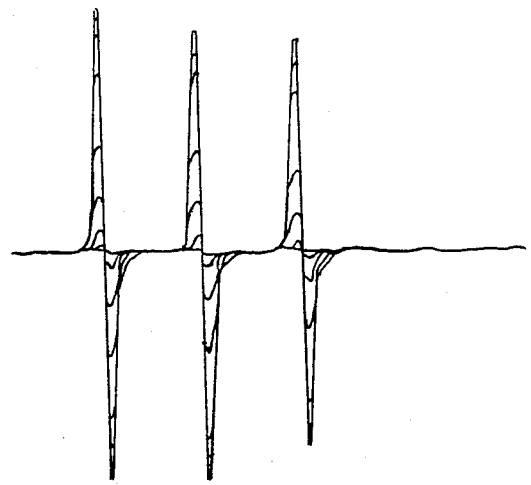
FIG. 3 depicts EPR spectra showing the progressive reduction of spin-labelled quat (2) by pure thioredoxin reductase.
Figure 4:
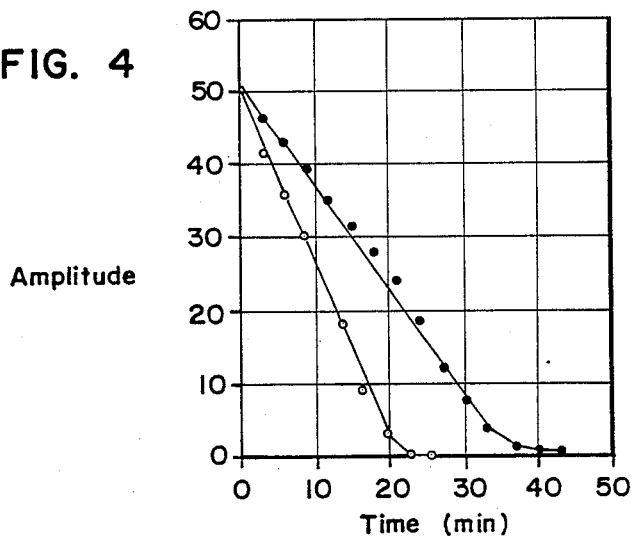
FIG. 4 graphically depicts the rates for the reduction of spin-labelled quat 2 by thioredoxin reductase (o-o) and by thioredoxin reductase plus thioredoxin (1:10) (●-●). Thioredoxin is an effective competitive electron acceptor to spin-labelled quat (2).

Under these conditions, thioredoxin reductase was found to rapidly reduce spin-labelled quat (2) without leaving any residual proteincomplexed paramagnetic substrate (FIG. 4). This result is in contrast to the reaction of this substrate at the surface of keratinocyte membranes in vivo where a considerable fraction remains complexed (FIGS. 1A and 2). Binding occurs on the outer cell layer of the eipdermis and on the outer surface of the plasma membrane of cultured human keratinocytes. It appears that "ion-pair" formation with receptor sites on the surface of keratinocytes provides a thermodynamically stable complex which must be in slow exchange, otherwise complete reduction of the spin-labelled quat by thioredoxin reductase would occur in vivo as it does in vitro.

FIG. 4 shows that thioredoxin effectively competes for electrons with the spin-labelled quat. This result indicates that in the presence of radicals, the concentration of oxidized thioredoxin increases, whereas the absence of radical substrate should promote internal electron transfer to push the reaction in the direction of thioredoxin reduction.

Since a direct correlation between UV-irradiation, radical concentration and melamin biosynthesis has been established, and since keratinocytes as well as melanocytes contain high concentrations of thioredoxin, the effect of oxidized and reduced thioredoxin on tyrosinase activity was determined.

Figure 5:
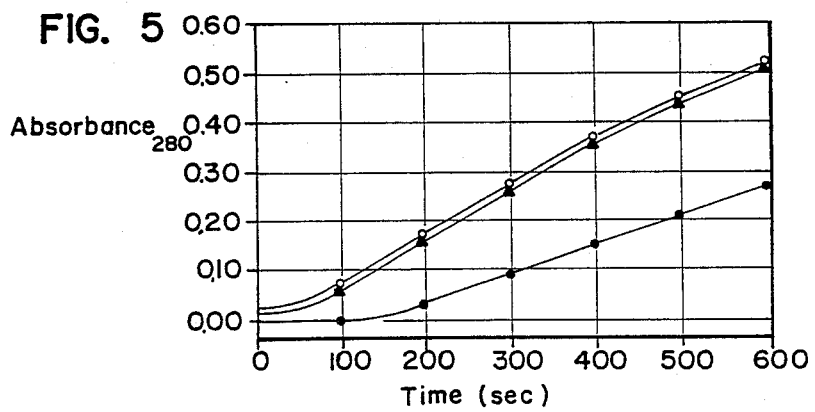
FIG. 5 graphically depicts the effect of oxidized (o-o) and reduced (●-●) thioredoxin on tyrosinase activity as compared with a tyrosinase control (▲-▲).

FIG. 5 demonstrates that oxidized thioredoxin in a ratio of 10 to 1 over tyrosinase has no effect on the oxidation of 10 μmoles of L-tyrosine to dopaquinone.

However, when the same concentration of reduced thioredoxin is generated by NADPH/thioredoxin reductase, tyrosinase activity is regulated down to 58% of the oxidized thioredoxin control. This represents a substantial inhibitory effect considering that regulation of enzyme activity occurs through protein-protein interaction.

The invention has been described with reference to various specific and preferred embodiments and techniques. However, it should be understood that many variations and modifications may be made while remaining within the spirit and scope of the invention.

What is claimed is:

1. A method for measuring the activity of thioredoxin reductase in mammalian cells comprising:
   (a) contacting the cells with a hydrophobic quaternary ammonium salt comprising a stable nitroxide free radical spin label;
   (b) measuring the rate of reduction of the free nitroxide free radical of the uncomplexed quaternary ammonium salt at the cell surface by electron spin resonance spectroscopy; said rate of reduction providing a measure of thioredoxin reductase activity at the surface of the cells 2. The method of claim 1 wherein the cells are epidermal cells.

3. The method of claim 1 wherein the cells are melanocytes.

4. The method of claim 3 wherein the cells are malignant melanocytes.

5. The method of claim 1 wherein the quaternary ammonium salt is a halogen salt of 3-(dimethyl-benzylamino) acetamido-2,2,6,6-tetramethylpiperidine-N-oxyl.

* * * * *

UNITED STATES PATENT AND TRADEMARK OFFICE
CERTIFICATE OF CORRECTION

PATENT NO. : 4,849,346

DATED : July 18, 1989

INVENTOR(S) : J. Wood et al.

It is certified that error appears in the above-identified patent and that said Letters Patent is hereby corrected as shown below:

Col. 1, line 27, for "OH· and $O_2^-$" read --$OH^\bullet$ and $O_2^{\cdot-}$--.

Col. 2, line 14, for "spinlabelled" read --spin-labelled--.

Col. 2, lines 29 and 31, for "$O_2^-$" read --$O_2^{\cdot-}$--.

Signed and Sealed this

Seventh Day of August, 1990

Attest:

HARRY F. MANBECK, JR.

Attesting Officer

Commissioner of Patents and Trademarks